United States Patent [19]

Levinson et al.

[11] 4,227,333
[45] Oct. 14, 1980

[54] METHOD FOR THE EARLY DETECTION, LOCALIZATION AND CONTROL OF KHAPRA BEETLES AND THEIR LARVAE, AND AN ODOR, TASTE AND/OR CONTACT-RESPONSIVE TRAP FOR CARRYING OUT THE METHOD

[76] Inventors: Hermann Levinson; Anna-Rose Levinson, both of Oberholzstrasse 4, 8131 Starnberg, Fed. Rep. of Germany; Wendell Burkholder, University of Wisconsin, Madison, Wis. 53706; Robert M. Silverstein; Robert Cassidy, both of State University of N.Y., Syracuse, N.Y. 13210

[21] Appl. No.: 837,648

[22] Filed: Sep. 28, 1977

[30] Foreign Application Priority Data

Sep. 30, 1976 [DE] Fed. Rep. of Germany ....... 2644217

[51] Int. Cl.³ .............................................. A01M 1/00
[52] U.S. Cl. ...................................... 43/107; 43/121; 43/131; 43/132 R
[58] Field of Search ................. 43/107, 121, 123, 131, 43/132 R, 133

[56] References Cited

U.S. PATENT DOCUMENTS

| 2,177,670 | 10/1939 | Peirson | 43/107 |
| 2,315,772 | 4/1943 | Closs | 43/121 |
| 3,304,646 | 2/1967 | Staley | 43/114 X |
| 3,747,260 | 7/1973 | Louness | 43/132 R |
| 3,866,349 | 2/1975 | Meijer | 43/114 |
| 3,913,259 | 10/1975 | Nishimura | 43/121 |
| 3,972,993 | 8/1946 | Kobayashi | 43/131 |

FOREIGN PATENT DOCUMENTS 781707 8/1976 United Kingdom .................. 43/132 R Primary Examiner—Nicholas P. Godici
Attorney, Agent, or Firm—Gilbert A. Thomas

[57] ABSTRACT

A contact and odor responsive device for trapping khapra beetles and their larvae in which fibrous paper or fabric strips are constructed to provide contact allowing forms containing pheromone attraction means, food attractive means and lethal means for destroying the beetles and a method of using said traps to detect and destroy the beetles and their larvae.

1 Claim, 3 Drawing Figures

U.S. Patent     Oct. 14, 1980     4,227,333
FIG. 1
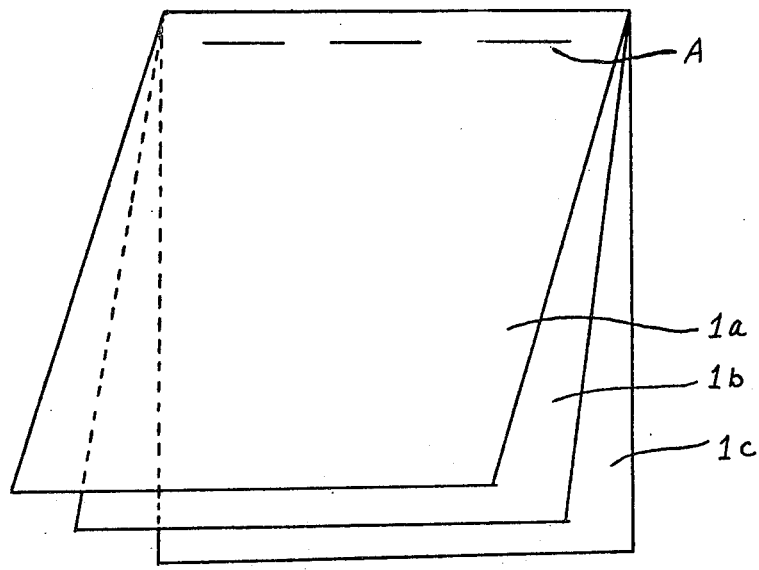
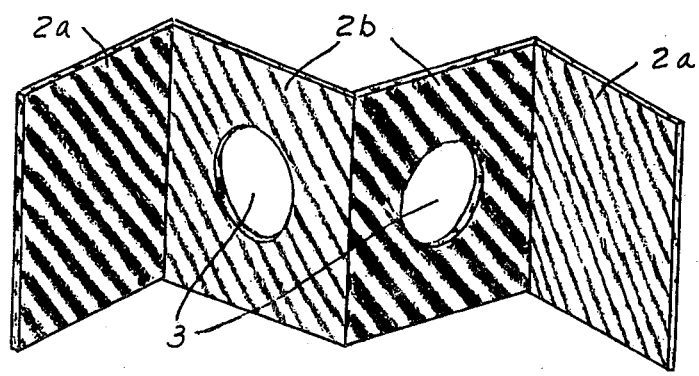
FIG. 2A
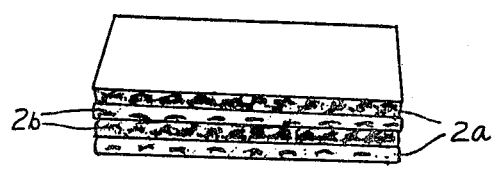
FIG. 2B

METHOD FOR THE EARLY DETECTION, LOCALIZATION AND CONTROL OF KHAPRA BEETLES AND THEIR LARVAE, AND AN ODOR, TASTE AND/OR CONTACT-RESPONSIVE TRAP FOR CARRYING OUT THE METHOD

A method for the early detection, localization and control of Khapra bettles and their larvae, and an odor, taste and/or contact-responsive trap for carrying out the method.

The Khapra beetle Trogoderma granarium (Everts) is one of the most serious pests encountered in the storage and transportation of cereals and grains. Control of this beetle is difficult because it is characterized by small size, an inconspicuous color, good adaptability to changes in climate as well as by the ability to remain in the larvae stage for years if there is lack of food and under other adverse conditions. A further factor making its control difficult is that the larvae can live in crevices and gaps in the walls, floors and ceiling of the store room and can penetrate to a depth of about 10 centimeters and survive there for extended periods. The Khapra beetle is a particularly serious pest not only in countries with a dry and warm climate, but also in Central Europe, where it was introduced with imported foodstuffs and has already done considerable damage particularly in malt store rooms.

This pest of stored food cannot satisfactorily be combated with conventional control measures. Insecticides, with which the stored material is usually gassed at regular intervals, can only be used within limits because of the high costs involved, the enormous adaptability of the beetles, the increase in the resistence of the insects, and because of detrimental residues that form on the treated products that are harmful to humans and animals and result in adverse environmental effects. Despite these drawbacks, gassing of the stored material with pesticides is the most conventional method of pest control, and frequently it is employed as a purely preventive measure in cases where pest infestation does not yet exist.

The object of this invention is to provide ways and means by which Khapra beetles and their larvae can be detected in store rooms and can be combated in a manner that is particularly simple, less expensive, very effective and completely harmless to the environment and man.

The invention is based on the knowledge that the problem as stated can be solved if devices of textile and paper strips of a unique construction are employed as a trap, in combination with luring agents as these traps will serve as infestation monitor for the routine quarantine testing of imported goods. As traps they will also be effective in depleting or preventing the growth of the insect population, or with the addition of pathogens can act as insect killing devices.

The object of the invention is thus a method for the early detection, localization and control of Khapra beetles and their larvae in cereal or grain situations, which is characterized in that strip portions of textile or paper material having a fibrous surface, which are disposed closely adjacent one another forming slots and/or tubes, are set out at the locations of the store situations to be checked for pest infestation or to be treated against pest infestation, in a manner so that they are accessible to the pest insects, the number of pest insects collected in the strip portions during a selected time interval is determined and, if the result is positive, strip portions of the indicated type are set out and renewed purposefully and as a matter of routine, and the pest insects that have in each case collected thereon are destroyed, optionally together with the strip portions.

The object of the invention is also an odor, taste and/or contact-responsive trap device for Khapra beetles and their larvae, which is characterized in that it consists of a plurality of strip portions of textile or paper materials having a fibrous surface, which are disposed closely adjacent to one another in a manner such that slot and/or tube-configured spaces are of a size to lure the insects by contact stimulation are formed therebetween.

The invention will be described in more detail with reference to the accompanying drawing, in which:

FIG. 1 is a perspective diagrammatic view of a trap made of textile materials.

FIG. 2a is a perspective view of a corrugated paper strip adapted to be folded together to form a trap, before said strip is folded together, and FIG. 2b is a perspective view of the corrugated paper strip after said strip has been folded together to form the trap.

The trap shown in FIG. 1 is made from three pieces of fabric 1a, 1b and 1c, that are stitched together along the edge A, and which consist of materials having a fibrous surface, e.g. sack-cloth (jute), felt or cotton, and which may be of widely varying sizes. We have found that pieces of fabric about 10 centimeters in width and a length of 11 centimeters have proved most suitable. Luring agents and/or pesticides are preferably applied to the center of the central fabric piece 1b. The surface property of the fabric employed promotes a massive accumulation of the larvae and adult Khapra beetle, which are thignotactically disposed, i.e., take their orientation according to their tactile sense. Traps of this type may of course also consist of more than three such pieces of fabric. These traps are usually simply placed on the location to be checked, e.g., on the stored material, although they may also be suspended if their lower end is in contact with the stored material.

The trap shown in FIGS. 2a and 2b is formed of a corrugated paper strip having three folding creases, which make it possible to fold up said strip in such a manner that two cover sections 2a and two central sections 2b result. Thus, an inner cavity is formed by the recesses 3 of the central sections 2b, which allows for the accumulation of numerous beetles and their larvae. This inner cavity is accessible to the pest insects via the tubes present in the corrugated paper as well as via the tube that are formed by the peaks and valleys of the corrugated paper when it is folded. The luring agents and/or pesticides are preferably applied to the center of the trap, i.e., in the region of the inner cavity (3). The traps when folded up and ready for use as shown in FIG. 2b can be held together by means of a simple rubber band or by means of a string. Traps of this type are simply placed at selected locations of the storage areas or on the storage material to be checked or to be treated against pest attack.

Destruction of the insect pests that have collected in the trap is done in the usual known manner, e.g. with the aid of hot water, steam or hot air. Because of the low cost of the traps they are usually destroyed with the traped insects.

It has proved to be of particular advantage to provide the traps with the pheromone secreted by azygous khapra beetle females, the primary component of which has recently been discovered and synthetized. This is (Z)-14-methyl-8-hexadecenal (termed Z-trogodermal below) and (E)-14-methyl-8-hexadecenal (E-trogodermal). When using the synthetic products, they are usually dissolved in a volitile solvent, e.g. hexane, and are applied to simplify application in drops to the center of the traps. The traps are ready for use after the solvent has volatilized. It is also possible to use, besides the synthetic products, extracts recovered from the khapra beetle female using a suitable solvent, e.g. hexane. The application of such extracts has an effect analogous to that of the synthetic product solutions.

The traps which have been thus prepared with the pheromone from the female as bait lure not only the khapra beetle males but also the females of the khapra beetle. However the dosage needed to attract females must be several times the concentration needed to attract the males. This indicates that for females the scent is not a definite sex luring agent but is rather a "collecting scent". The beetles thus attracted crawl between the fabric layers and/or hollow spaces and remain there for days at rest because of the continual contact stimulation they receive from the fibrous surface of the materials of the trap as well as by the hairy surfaces of the bodies of other beetles.

The beetle larvae also are attracted for long periods of time into the gaps and hollow spaces of traps even if no pheromones are used. The number of such allured larvae can be substantially increased by using feed luring agents. Straight-chain fatty acids, in particular valeric acid, have proved particularly effective luring agents.

The combined use of pheromone and feed luring agents makes it possible to bait these pests in all their movable life stages, and since a far greater percentage of males than females, besides larvae, can be attracted and destroyed, there is the possibility of reducing such pest population or at least preventing the growth of the population. According to this embodiment of the invention, the traps act in the manner of an insectistatic agent and may be designated as combined odor, taste and contact-responsive traps.

It is also possible according to the teaching of this invention to achieve an insecticide effect aimed at the total extermination of the pests if the said combined odor, taste and contact-responsive trap is additionally provided with pathogens which spread a nidus throughout the pest population. A typical pathogenic organism suited for this purpose is e.g. Mattesia Trogodermae Canning.

The invention is described in more detail by the following examples.

EXAMPLE 1

This example shows the influence of the surface property of the materials used to construct the traps has on the luring effect.

100 females (W), 100 males (M) as well as 100 larvae (L) of the khapra beetle Trogoderma granarium were used in each test. The distribution of the pests that went into the traps within 24 hours was determined. Besides unbaited traps (b) used for comparison purposes, baited traps (a) were used that were charged in each case with 100 ug of synthetic (Z)-trogodermal. The results obtained (expressed in percent) are given in table I below.

The indications "light" and "dark" as contained in the table refer to the light conditions existing in the test room. The indications "plain", "corrugated" and "tubes" refer to the structure of the paper materials used to produce the trap, "tubes" designating a corrugated paper having a tube-like construction.

TABLE I

| pest | | surface property of the trap | | | total number allured |
|---|---|---|---|---|---|
| | | plain | corrugated | tubes | |
| (a) provided with a luring agent | | | | | |
| M | light | 4.0 | 13.0 | 73.0 | 90.0 |
| M | dark | 0.0 | 18.0 | 70.0 | 88.0 |
| W | light | 8.5 | 26.5 | 54.5 | 89.5 |
| W | dark | 0.0 | 29.0 | 57.5 | 86.5 |
| L | light | 8.0 | 23.0 | 49.0 | 80.0 |
| L | dark | 1.0 | 14.0 | 45.0 | 60.0 |
| (b) not provided with a luring agent | | | | | |
| M | light | 4.0 | 12.0 | 23.0 | 39.0 |
| M | dark | 0.0 | 8.0 | 26.0 | 34.0 |
| W | light | 5.0 | 20.0 | 38.0 | 63.0 |
| W | dark | 0.0 | 20.0 | 32.0 | 52.0 |
| L | light | 9.0 | 22.0 | 49.0 | 80.0 |
| L | dark | 0.0 | 15.0 | 48.0 | 63.0 |

The results show that traps which include tubes, such as those of the type shown in FIGS. 2a and 2b, had by far the greatest effectiveness. It is, also, apparent that traps made according to the invention provided with a pheromone bait allured far more males than females. The number of allured males was somewhat less than that of allured females for the traps of the invention not provided with a luring agent. About the same number of larvae went into traps provided with luring agent and traps not provided with luring agent, indicating the pheromone has little effect on the larvae.

EXAMPLE 2

This example shows the attraction of male and female khapra beetles to traps of the type shown in FIG. 1 which may be used in small storage areas.

A trap provided with a luring agent and a trap not provided with a luring agent each were placed horizontally on the surface of stored wheat (10 kg), into which 300 unmated females and 300 unmated males (age from 2 to 3 days) had been introduced. A pheromone-extract from 100 to 125 unmated females freshly prepared using hexane as a solvent was used as luring agent, instead of synthetic pheromone. The traps were impregnated with said extract, as described above. The number of allured khapra beetles was recorded daily at about 3 p.m. The results obtained are listed in table II below, which reflects the number of male and female khapra beetles that went into the trap expressed as a percentage of the total beetles released.

Table II

| trap | day after test started | | | | |
|---|---|---|---|---|---|
| | 1 | 2 | 3 | 4 | 5 |
| with pheromone | 83 | 87 | 86 | 90 | 75 |
| without pheromone | 56 | 54 | 50 | 49 | 37 |

The results show that significantly higher and quicker luring rates were achieved with the traps provided with a luring agent than were achieved with the traps not so provided. The luring effect of the traps not provided with a luring agent is obviously based on the contact stimuli which said traps have, as well as on a secretion of a pheromone of the khapra beetle females which aggregated with the males.

The results further show that, starting from the fifth day, a substantial number of the beetles left the traps provided with a luring agent as well as also the traps not provided with a luring agent. We believe the explanation for this is that by that time copulation had taken place. The test was discontinued after the fifth day because it was not intended that this test was to study other than the pest attraction effect of the traps.

Corresponding results were obtained when the synthetically recovered Z-8-hexadecenal was used as luring agent. This compound is chemically closely related to the primary component of the natural pheromone, and despite the absence of the methyl group in the 14-position it surprisingly develops practically the same effect as Z-trogodermal while being, however, substantially less expensive.

We claim:

1. A contact and odor responsive device for trapping Khapra beetles and their larvae comprising in combination a feed luring means, a synthetic pheromone and a lethal means contained within a trap constructed of a corrugated paper board strip, which is folded together to form two cover sections and two center stations provided with recesses in a manner such that the recesses of the center sections define an inner cavity.

* * * * *